US008695599B2

(12) United States Patent
Friberg et al.

(10) Patent No.: US 8,695,599 B2
(45) Date of Patent: Apr. 15, 2014

(54) CONTROL VALVE FOR RESPIRATORY DEVICES

(75) Inventors: Harri Friberg, Mauren (LI); Jakob Daescher, Flaesch (CH); Michael Wirth, Truebbach (CH); Felix Kramer, St. Gallen (CH)

(73) Assignee: imtmedical ag, Buchs (CH)

( * ) Notice: Subject to any disclaimer, the term of this patent is extended or adjusted under 35 U.S.C. 154(b) by 1175 days.

(21) Appl. No.: 12/527,866

(22) PCT Filed: Feb. 5, 2008

(86) PCT No.: PCT/IB2008/050415
§ 371 (c)(1),
(2), (4) Date: Oct. 26, 2009

(87) PCT Pub. No.: WO2008/096316
PCT Pub. Date: Aug. 14, 2008

(65) Prior Publication Data
US 2010/0139656 A1    Jun. 10, 2010

(30) Foreign Application Priority Data
Feb. 5, 2007    (CH) .................................. 0184/2007

(51) Int. Cl.
*A62B 9/02*    (2006.01)
*A61M 16/00*    (2006.01)
*A62B 7/00*    (2006.01)

(52) U.S. Cl.
USPC ............ 128/205.24; 128/204.18; 128/204.23; 251/304

(58) Field of Classification Search
USPC ............ 128/200.24, 204.18, 205.24; 251/88, 251/160, 180, 192, 208, 283, 304, 212
See application file for complete search history.

(56) References Cited

U.S. PATENT DOCUMENTS 1,043,935 A * 11/1912 Hitchcock .................... 251/184
2,270,078 A    1/1942 Mueller
(Continued)

FOREIGN PATENT DOCUMENTS

DE    29922220 U1    8/2000
EP    621052 A    10/1994
(Continued)

OTHER PUBLICATIONS

English translation of International Preliminary Report on Patentability, dated Sep. 17, 2009, from International Application PCT/IB2008/050415 filed Feb. 5, 2008; 14 pages total.

(Continued)

*Primary Examiner* — Justine Yu
*Assistant Examiner* — Valerie L Skorupa
(74) *Attorney, Agent, or Firm* — George Kapsalas; Patentbuero Paul Rosenich AG

(57) ABSTRACT

The invention relates to a respiratory device for keeping a patient breathing artificially or support his or her breathing naturally. Said respiratory device comprises an air inlet, an air source, and at least one proportionally adjustable control valve. The control valve is provided with a housing (11) and a rotary valve (12) which is arranged in the housing so as to be twistable about the longitudinal axis thereof and which allows through-holes (11d) of the housing (11) to be entirely or partially closed by twisting the rotary valve (12). The rotary valve (12) and a corresponding support surface (11f) of the housing (11) have a conical shape, the support surface (11f) cooperating with the rotary valve (12). The through-holes (11d) are disposed in the area of the support surface (11f).

19 Claims, 4 Drawing Sheets

(56) References Cited

U.S. PATENT DOCUMENTS

Figure 1:
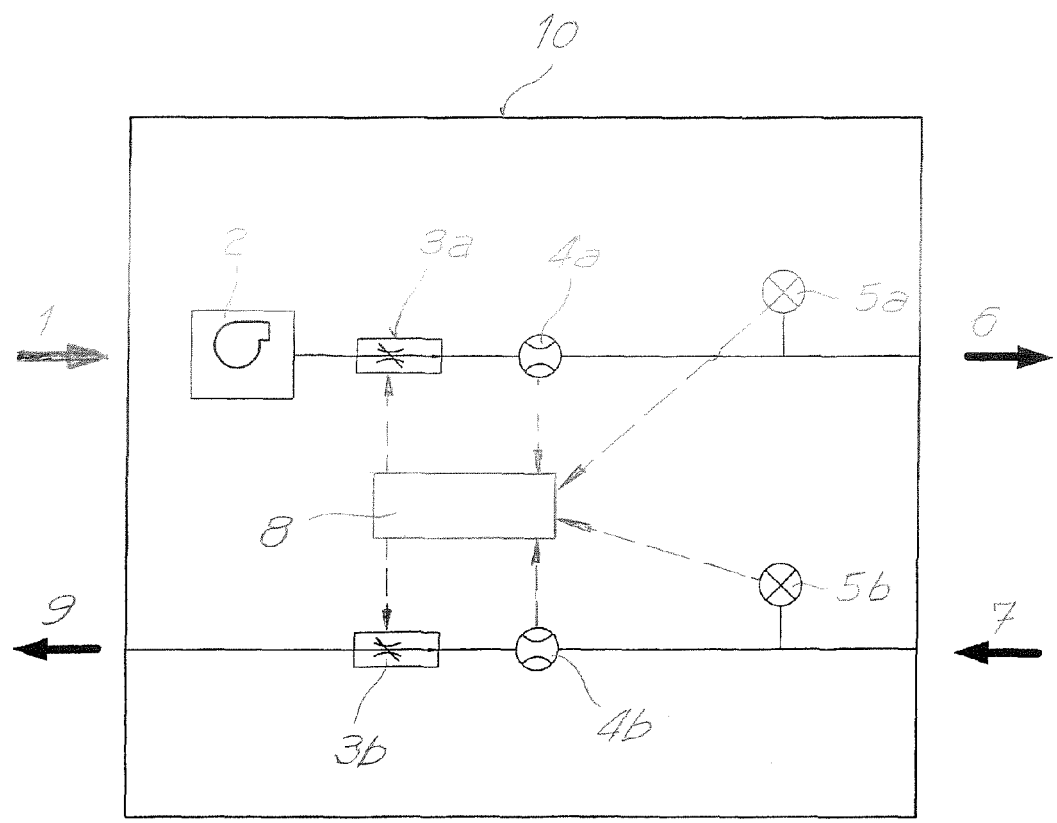

| | | | |
|---|---|---|---|
| 3,159,179 A | 12/1964 | DeLain | |
| 3,421,544 A * | 1/1969 | Bozoyan | 137/505.47 |
| 3,561,487 A * | 2/1971 | Reed, Jr. | 137/625.32 |
| 4,174,092 A * | 11/1979 | Macleod | 251/214 |
| 4,290,452 A * | 9/1981 | Takahashi et al. | 137/625.23 |
| 4,838,220 A * | 6/1989 | Parsons | 123/190.14 |
| 5,148,802 A | 9/1992 | Sanders et al. | |
| 5,211,370 A * | 5/1993 | Powers | 251/4 |
| 5,464,043 A | 11/1995 | Damia | |
| 6,148,816 A | 11/2000 | Heinonen et al. | |
| 6,182,657 B1 | 2/2001 | Brydon et al. | |
| 6,615,831 B1 | 9/2003 | Tuitt et al. | |
| 6,722,359 B2 | 4/2004 | Chalvignac | |
| 6,796,328 B2 * | 9/2004 | Myles | 137/557 |
| 7,040,318 B2 | 5/2006 | Dascher et al. | |
| 7,212,937 B2 | 5/2007 | Friberg | |
| 7,461,654 B2 | 12/2008 | Friberg et al. | |
| 7,735,517 B2 * | 6/2010 | Kerckhove et al. | 137/625.63 |
| 2006/0120886 A1 | 6/2006 | Friberg et al. | |
| 2006/0144163 A1 | 7/2006 | Friberg | |
| 2007/0107787 A1 * | 5/2007 | Moretz | 137/625.11 |
| 2009/0215017 A1 | 8/2009 | Friberg | |

FOREIGN PATENT DOCUMENTS

| | | |
|---|---|---|
| EP | 621052 A3 | 12/1994 |
| EP | 1177810 B1 | 3/2004 |
| GB | 288403 A | 4/1928 |
| GB | 352228 A | 7/1931 |
| GB | 924377 A | 4/1963 |
| GB | 2215218 A | 9/1989 |
| WO | 92/11054 A1 | 7/1992 |
| WO | 99/47839 A1 | 9/1999 |
| WO | 2004/045695 A1 | 6/2004 |
| WO | 2004/046661 A1 | 6/2004 |
| WO | 2006/056927 A1 | 6/2006 |
| WO | 2008/096316 A3 | 2/2009 |

OTHER PUBLICATIONS

PCT International Research Report for Application PCT/IB2008/050415 dated Nov. 7, 2008.

* cited by examiner

CONTROL VALVE FOR RESPIRATORY DEVICES

This application is a 35 U.S.C. 371(c) national-phase entry of PCT International appl. no. PCT/IB2008/050415 filed on Feb. 5, 2008, and claims the benefit of priority to prior Swiss national application no. CH-0184/2007 filed on Feb. 5, 2007.

The invention related to a valve for the flow control and regulation of a ventilator, the valve having a housing and a rotary slide valve arranged therein rotatable about its longitudinal axis, and by rotating the rotary slide valve at least one through hole is entirely or partially closable, and the rotary slide valve has a cone shaped sealing surface, which works together with a correspondingly designed support surface of the housing, and the through hole is arranged in the area of the sealing surface.

Ventilators are used in stationary (for example in the clinical or home environment) as well as in mobile locations (emergency medical services, for example). It is therefore very important that these devices function reliably and trouble free. In order to prevent environmental disturbances during the operation of such devices, these devices must be as quiet as possible during operation.

Document U.S. Pat. No. 6,615,831 discloses a ventilator with a 3/2-way valve. The valve has a control slide that is axially moveable by means of a magnet coil, which slide in its end position opens or closes through holes for the respirational air arising from a pressure generator while opening at the same time separate through holes in order to make a minimal air consumption possible for the pressure generator. However, this valve is very dependent on its location and, as a result, the radial play necessary for the axial moveability of the control slide is also leaky in its closed state.

Document EP 1177810B1 shows a valve with a rotary slide valve that is rotatable about its axis. This rotary slide valve has at least one longitudinal slit on its periphery that can be made to match with corresponding openings of the housing part that surrounds the slider. A control curve is moreover positioned on the free end face of the rotary slide valve by means of which curve the openings can also be only partially uncovered. This valve likewise has the disadvantage that it is never entirely sealed in the closed state. In order to ensure the dynamics of the valve, the rotary slide valve must be adjusted with a certain amount of radial play in the housing part. With the resulting annular gap, a part of the breathable air and thus the desired dosed amount can be negatively affected.

Document GB 288403A disclosed a valve or a slider for gases and other liquids. It has a housing with a conical seat and a valve body that is shaped like a truncated cone and can be externally actuated by rotation. Upon rotating the valve body, through holes in the conical seat of the housing are matched with openings on the valve body, thus making it possible for the medium to flow through the valve. The large area of surface contact of the valve body in the conical seat causes, however, a relatively high degree of friction resistance to arise that negatively affects the actuation and prevents dynamic control of the valve.

The object addressed by the invention is therefore to create a ventilator or a valve for a ventilator, that is operationally secure, has minimal flow resistance, is characterized by favorable dynamics, and when in a closed state makes a high degree of leak tightness possible.

According to the invention, this is achieved in that the rotary slide valve is supported in the axial direction over a central touching point, preferably a ball arranged in the longitudinal center line on the housing. A touching point between the rotary slide valve and the housing produces minimal friction losses and thereby makes favorable dynamics possible by means of small actuating forces and actuating torques. Owing to the conical sealing surface, upon closing the valve, the rotary slide valve is pressed against sealing surface by means of the over pressure of the inhalation or exhalation air. Losses dues to leaks are practically avoided because of this. Wear of the rotary slide valve and the corresponding support surfaces owing to wear and tear are automatically compensated.

The ball of the sealing surface is advantageously designed to taper against the direction of flow. When the ball is flowed against by the inhalation or exhalation air, a uniform distribution of the air current in the valve results, as does a relatively smaller resistance to flow.

The angle of taper of the sealing surface is advantageously between 60° and 120°, preferably approximately 90°. This angle of taper permits a relatively short and compact construction of the valve. Said angle of taper also produces favorable flow ratios and extensive prevention against turbulence.

The through holes are advantageously designed in such a manner that upon rotating the rotary slide valve in the closed direction, the through flow cross section progressively become smaller and/or a plurality of through holes are provided. At the end of the closing proves, only a very small through cross section exists in such a manner that upon complete closure of the valve, pressure blows in the system can be largely avoided. If there is a plurality of bore holes, they can be of different sizes, wherein the sizes of the bore holes grow smaller toward the end of the closure process. The same effect can be achieved in that a plurality of bore holes are arranged side by side in the radial direction and the number of the bore holes that are arranged radially one beside the other decreases toward the end of the closure process.

The through holes are advantageously designed as conically tapering in the closure direction of the rotary slide valve. The shape of the cone can effect that the remaining flow through cross section more quickly or more slowly diminishes or enlarges in size during the closing of the valve. The edges of the cone shaped through-hole are preferably designed as curved.

In order to achieve favorable dynamics and a good seal of the valve in the closed state, it is necessary that the radius of the cone of the sealing surfaces, which work together, of the housing and/or of the rotary slide valve constantly increases against the direction of closing of the valve over parts of the periphery. The sealing surfaces that abut one another of the rotary slide valve and of the housing are thus not precise conical surfaces but rather deviate only slightly from a cone shaped surface according to this special configuration. In the closed state of the valve, the sealing surfaces planarly support one another, resulting in a very solid seal. Upon opening the valve, a seal gap results that additionally increased the through flow cross section and thus makes a greater flow through the valve possible.

A further advantageous embodiment consists in that the through holes of the housing on the side opposite the rotary slide valve are surrounded by a bead, the edge height of the bead increasing against the closure position of the valve. In this manner, a surface seal likewise results in the closed state of the valve. Upon opening the valve, the rotary slide valve is raised from the bead that likewise causes an additional sealing gap to result.

Yet another useful design of the valve consists in that it has a completely or partially closable opening upon rotation of a rotary slide valve, the rotary slide valve being designed in the style of an iris diaphragm with lamellae that can be made to pivot in the clear cross section of the through hole by means of a rotatable rotary slide valve. The iris diaphragm has heretofore mainly been used in the field of optics in photographic and video cameras for the control of light.

An important goal of the invention also consists in making it possible to achieve as laminar a flow as possible within the valve. The lamellae are therefore advantageously moveable against a centrally arranged against a displacement body. Upon opening the valve, the displacement body is flowed around on all sides and thereby forms a so-called "swimmer" in the air current.

In order to make a solid seal of the valve possible by means of the approximately radially running lamellae, the displacement body can itself consist of an elastic material. However, it is necessary that the displacement body has at least an elastic sealing element.

The control valve is advantageously proportionally controlled by means of an actuating element, preferably by means of a step motor. Thus there are not only two final positions of the valve during operation, namely "open" or "closed", but also any intermediate positions can be actuated if the need arises.

A detachable, elastic coupling is advantageously arranged between the rotary slide valve and the actuating element. This coupling makes possible a play free transmission of the rotation movement from the actuating element to the rotary slide valve. At the same time, a possible offset can be balanced.

For an automatic restoration to its starting position, the rotary slide valve is advantageously rotatable against the restoration force of at least one torsion spring. In a flowless state of the rotary slide valve, a defined starting position thus exists. With a loss of power, the valve thus is or goes automatically preferably into a completely open position in such a manner that the natural breathing of the patient is not prevented.

The valve according to the invention is preferably used in an automatic ventilator for the artificial breathing or support of the breathing of the patient, with an air inlet, an air source, at least one proportionally regulatable control valve as well as sensors for measuring the pressure and the flow for controlling the control valve.

The air source in such a ventilator is advantageously designed as a rotating bellows with a constant rate of speed over an entire breathing cycle. Such a bellows is characterized by a high degree of quiet running as well as by a low noise level. The regulation of the breathing occurs through the control of the valve.

Further embodiments of the invention are given in the Figures and in the entirety of disclosure.

The reference number list is, as is the wording of the claims, subject matter of the disclosure.

Figure 2:
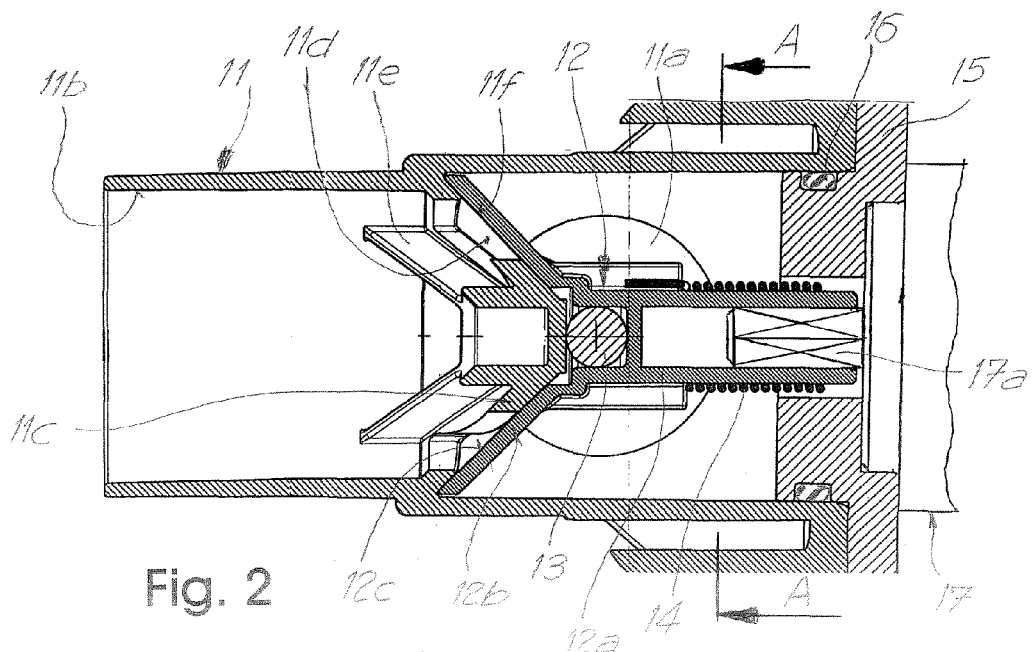
Figure 3:
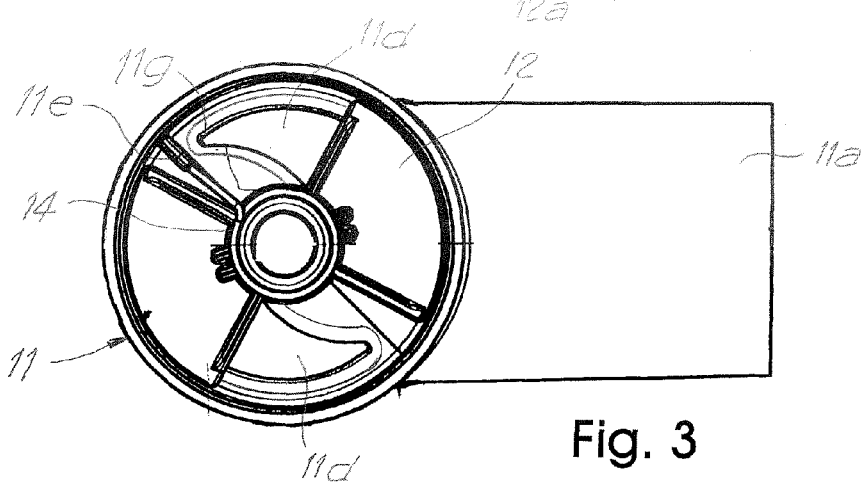
Figure 4:
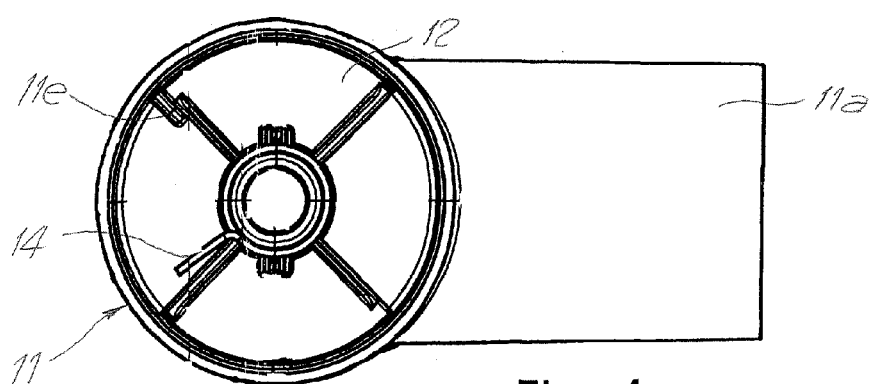
Figure 5:
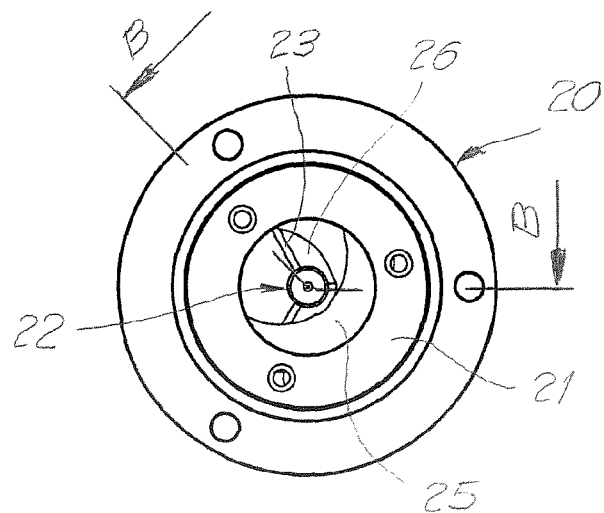
Figure 6:
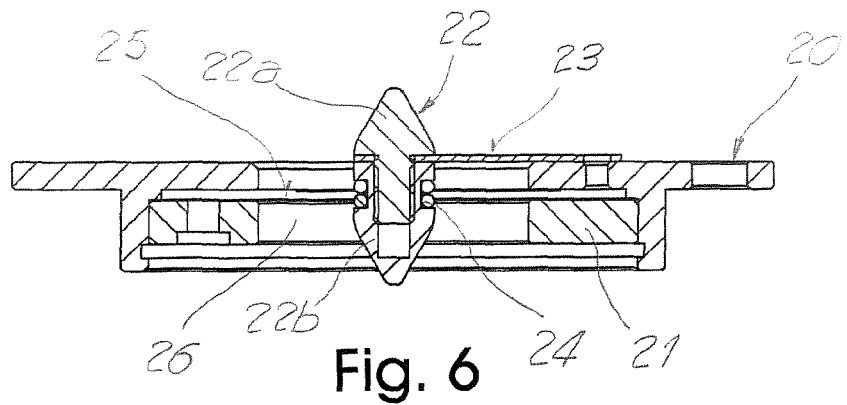
Figure 7:
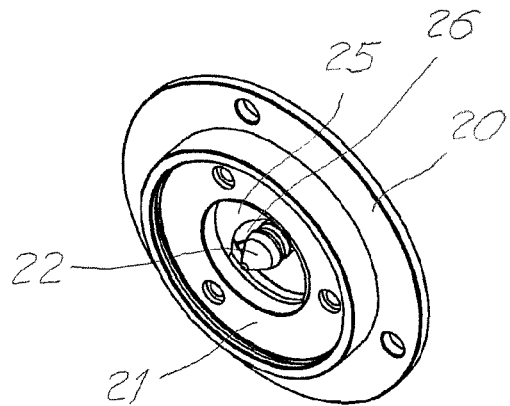
Figure 10:
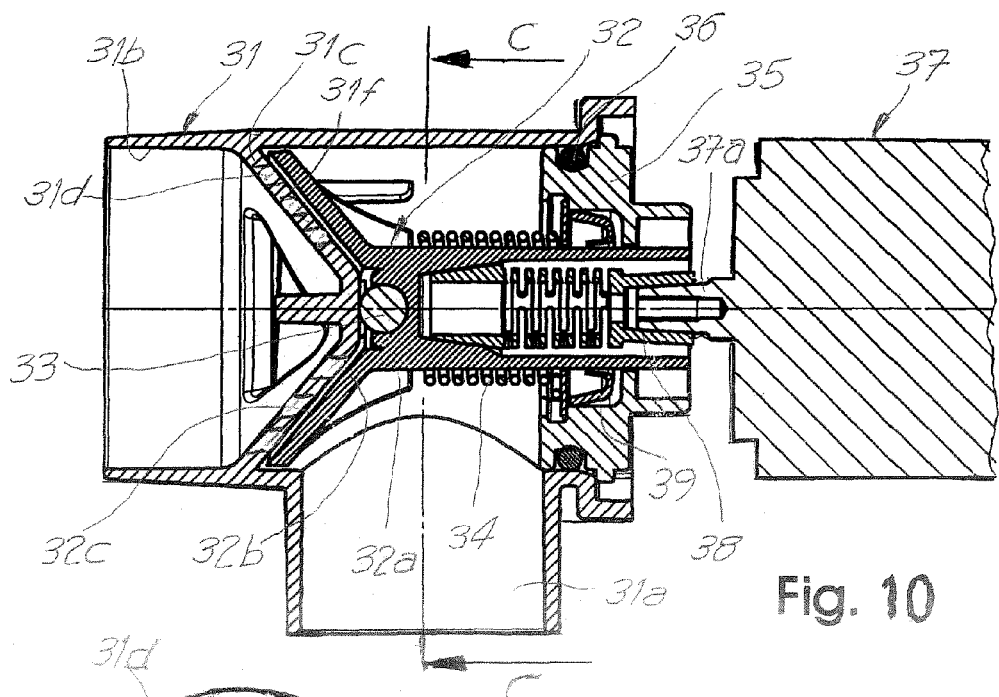
Figure 8:
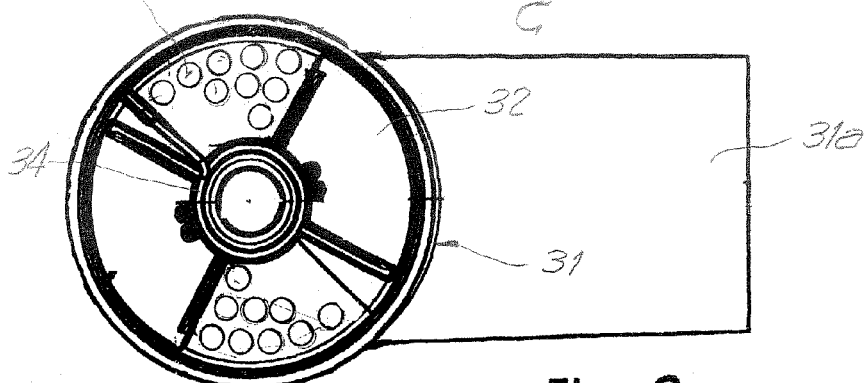
Figure 9:
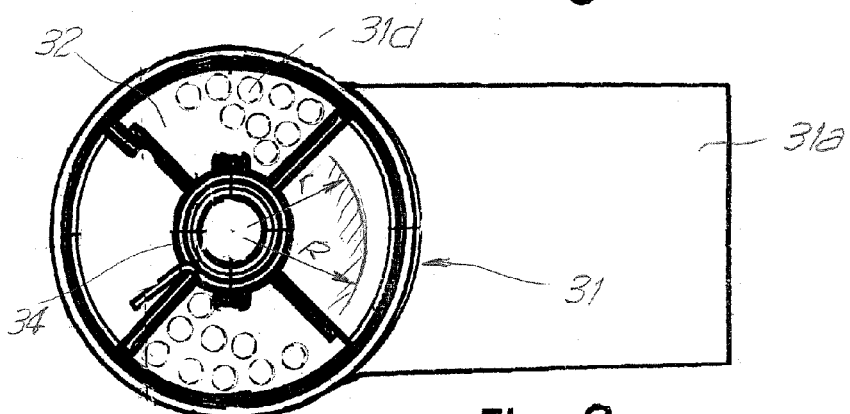

The Figures will be described coherently and comprehensively. The same reference numbers denote the same components, and reference numbers with different indices indicate functionally equivalent components. The invention is more closely explained symbolically and by way of example in the Figures, which show in:

FIG. 1: a schematically represented ventilator according the invention,

FIG. 2: a longitudinal section of a first embodiment of the ventilator according to the invention with a cone-shaped valve seat FIG. 3: a cross section through the valve shown in FIG. 2 along the line of intersection A-A and in the open state, FIG. 4: a cross section analogous to that of FIG. 3, in the closed state, FIG. 5: a front view of a further embodiment of the valve according to the invention designed in the style of an iris diaphragm, FIG. 6: a sectional drawing through the valve according to FIG. 5, along the line of intersection B-B, FIG. 7: a perspective view of the valve represented in FIGS. 5 and 6, FIG. 8: a cross section along the line of intersection C-C in FIG. 10 through a further design of the valve according to the invention in an open state, FIG. 9: the valve according to FIG. 8 in the closed state, FIG. 10: a longitudinal section through the valve visible in FIGS. 8 and 9.

The ventilator, which is schematically shown in FIG. 1 and is provided with a casing 10 for protection, has an air inlet 1 and an air source 2. The air source 2 is preferably designed as a bellows or compressor. An internal or an external air accumulator or an external compressed air supply can also be used as an air source 2. An regulatable inhalation control valve 3*a*, a flow through sensor 4*a* for the inhalation, and a pressure sensor 5*a* for the inhalation are arranged in the upper line that serves as the inhalation of the patient. An inhalation tube 6 at the end of this line leads to the patient. An exhalation tube 7 leads from the patient back into the casing 10. A pressure sensor 5*b* for the exhalation, a flow through sensor 4*b* for the exhalation, and a regulatable exhalation control valve 3*b* are likewise arranged in this lower line that controls the exhalation. The measured values of the flow through and pressure sensors are continually fed to a control unit 8 where they serve to regulate the control valves 3*a*, 3*b* for the inhalation or the exhalation of the patient. Finally, the exhaled breathable air is released into the external environment via an air outlet 9.

The ventilator can be operated directly from an external power network or by means of an internal or external battery.

The embodiment of a control valve shown in FIGS. 2 to 4 consists of a housing 11 with a rotary slide valve 12 that is rotatably mounted therein. The housing 11 has a lateral inlet connection 11*a* and an outlet connection 11*b* that is connected to the rotary slide valve 12 in an axial direction. Between the inlet connection 11*a* and the outlet connection 11*b* is an intermediate wall 11*c*. The intermediate wall 11*c* is designed to have a cone like shape and includes an angle of taper of approximately 90°. The intermediate wall 11*c* is provided with wedge-shaped through holes 11*d*. The rotary slide valve 12 consists of a tubular shaft 12*a* and a hopper 12*b* connected thereto. The interior of the hopper 12*b* forms together with a support surface 11*f* a sealing surface 12*c* on the intermediate wall 11*c* of the housing 11, which sealing surface seals the through holes 11*d* in the valve in the closed state shown in FIG. 4.

As can be seen from FIG. 2, the rotary slide valve 12 is centrally supported in the axial direction atop a ball 13 on the housing 11. The ball 13 yields a on both parts 11, 12 a central touching point in the area of the longitudinal center line and thus makes possible very minimal friction.

A torsion spring 14, which surrounds the shaft 12*a* of the rotary slide valve 12, serves to hold the rotary slide valve 12 in a defined starting position (for example "open" or "closed") when the valve is receiving no power. Moreover, the torsion spring 14 supports keeping the seal of the rotary slide valve 12 solid in that the hopper 12*b* is pressed against the intermediate wall 11*c* in the axial direction. A cover 15 is connected with the housing 11 on the side that is opposite the outlet connection 11*b*. A sealing ring 16, which is preferably designed as an "O" ring, serves to seal the cover 15.

A step motor 17 that serves as an actuating drive is fastened to the cover 15. The step motor 17 serves as the rotary drive of the rotary slide valve 12 by means of a drive shaft 17*a*. An over pressure is generated behind the valve upon closing the valve, which over pressure presses the hopper 12*b* or the sealing surface 12c of the rotary slide valve 12 axially against the support surface 11f of the housing 11. It is in this manner that practically no losses from leaks result. This makes it possible to operate an air source, which is designed as a bellows, for example, with a constant speed throughout an entire breathing cycle consisting of inhalation and exhalation. The entire dynamics of the breathing cycle can accordingly be achieved with solely the control valves. Guide vanes 11e in the longitudinal direction are intended to prevent turbulence in the flow in the valve. These guide vanes, however, are optional and thus can also be dispensed with.

As can be seen in FIG. 3, the through holes 11d are designed as cone shaped with curved edges. This shape makes it possible for a certain progressive, for example, closing or opening characteristic of the valve. In particular, pressure spikes can thus be decreased or prevented. In order to close the valve, the rotary slide valve 12 is rotated by means of the force of a torsion spring 14 into the closed position shown in FIG. 4. According to the air requirement, the through holes 11d can also be only partially opened by a smaller pivoting angle of rotary slide valve 12.

The through holes 11d are surrounded by a bead 11g. The edge height of the bead 11g is preferably increasing in the direction of closing. Thus, a run up slope is formed for the rotary slide valve 12. This enables a particular good seal to be achieved when the valve is in the closed state. Upon opening the valve, the rotary slide valve 12 can be raised from the bead 11g in such a manner that an additional sealing gap is opened and the throughput of the valve is increased.

The embodiment of the valve shown in FIGS. 5 to 7 has a housing 20 designed as a flange. An actuating ring 21 is rotatably mounted in the housing 20. A centrally arranged displacement body 22 is connected with the housing 20 by means of radial webs 23. The displacement body 22 consists of a cone shaped front part 22a and a cone shaped rear part 22b that are screwed together, for example. Lamellae 25 are pivotably fastened to the housing 20, which lamellae can be pivoted radially inward by means of rotating the actuating ring 21 according to the principle from the field of optics of a iris diaphragm. The displacement body 22 thus forms the radial catch of the lamellae 25. In order to obtain a good seal and to prevent damage to the lamellae 25, the displacement body 22 is provided with one or a plurality of elastic sealing elements 24 in the run up area of the lamellae 25. These sealing elements 24 can be designed as "O" rings for example. This control valve designed in the style of an iris diaphragm produces very favorable flow ratios through the symmetric arrangement of the through holes 26.

The valve shown in FIG. 8 to 10 functionally corresponds substantially to the embodiment shown in FIGS. 2 to 4 and likewise consists of a housing 31 and a rotary slide valve 32 rotatably mounted therein. The housing 31 has an inlet connection 31 is formed laterally on the housing 31. An outlet connection 31b is arranged coaxially to the longitudinal axis of the rotary slide valve 32. A cone shaped intermediate wall 31c is arranged between the inlet connection 31a and the outlet connection 31b. The intermediate wall 31c forms a support surface 31f for the rotary slide valve 32. The rotary slide valve 32 has a substantially cylindrical shaft 32a and a hopper 32b connected thereto. Sealing surfaces 32c are arranged in the area of the hopper 32b, which sealing surfaces together with the support surfaces 31f form a planar seal.

The rotary slide valve 32 is supported in a point shaped manner on the housing 31 over a centrally arranged ball 33 and is thus rotatable against very minimal resistance. A torsion spring 34 holds the rotary slide valve 32 in the starting position shown in FIG. 8. In this manner, the through holes 31d of the housing 31 are completely open and make flow through the valve possible. In contrast to the design shown in FIGS. 2 to 4, which have on both sides only one single cone shaped through hole (11d), in this configuration the through holes 31d are designed are a plurality of individual bore holes. The bore holes are arranged in such a manner that the flow through cross section likewise progressively decreases in the direction of closing.

The rearward end of the valve is closed by a cover 35. A sealing ring 36 is provided for creating a seal between the housing 31 and the cover 35. A shaft seal 39 that works together with the shaft 32a of the rotary slide valve 32 prevents the ventilator from having losses from leaks while simultaneously preventing the penetration of foreign matter.

The rotary slide valve 32 is likewise driven by means of an actuating drive such as a step motor 37 for example. The drive shaft 37a of the step motor 37 is accordingly connected to the rotary slide valve 32 by means of a detachable, elastic coupling 38. The flexibility of the coupling 38 produces at least three advantageous effects:

1. The rotation is transmitted from the step motor 37 free of play to the rotary slide valve 32.
2. A possible offset is balanced between the step motor 37 and the rotary slide valve.
3. The coupling can apply an additional axial force that leads to the rotary slide valve end of the coupling 38 continually fitting closely in the receptacle of the rotary slide valve 32.

In contrast to the design shown in FIGS. 2 to 4 in which the support surfaces 11f and the sealing surfaces 12c are designed as a precise cone, the sealing surface 32c and the support surface 31f have a variable cone radius r/R over the circumference, said radius continually increasing counter to the direction of closing. The helix angle of the radius change is preferably 3°. In this manner, it can be achieved that when the valve is in the closed state, the ball 33 is raised from the point touching and the sealing surfaces are axially pressed one against the other. This makes it possible for a solid seal of the valve in the closed state to be achieved.

Both the housing 11, 31 as well as the rotary slide valve 12, 32 are composed preferably of plastic. Plastics have a relatively minimal weight, thus resulting in a minimal net weight of the movable parts, in particular of the rotary slide valve 12, 32. On the other hand, this makes possible a high degree of dynamics in the movement of these parts. A further advantage of plastics consists in the fact that they are long lasting and are very conducive to sterilization.

REFERENCE NUMBER LIST

1 Air inlet
2 Air source
3a Inhalation control valve
3b Exhalation control valve
4a Flow through sensor for breathing
4b Flow through sensor for exhalation
5a Pressure sensor for breathing
5b Pressure sensor for exhalation
6 Breathing tube
7 Exhalation tube
8 Control
9 Air outlet
11 Casing
11a Inlet connection
11b Outlet connection
11c Intermediate wall
11d Through holes
11e Guide vanes 11f Support surface
11g Bead
12 Rotary slide valve
12a Shaft
12b Hopper
12c Sealing surface
13 Ball
14 Torsion spring
15 Cover
16 Sealing ring
17 Step motor
17a Drive shaft
20 Housing
21 Actuating ring
22 Displacement body
22a Front portion
22b Rear portion
23 Web
24 Sealing element
25 Lamella
26 Through hole
31 Housing
31a Inlet connection
31b Outlet connection
31c Intermediate wall
31d Through holes
31f Support surface
32 Rotary slide valve
32a Shaft
32b Hopper
32c Sealing surface
33 Ball
34 Torsion spring
35 Cover
37 Step motor
37a Drive shaft
38 Coupling
39 Shaft sealing ring

What is claimed is:

1. A flow control valve comprising:
a housing, said housing having an inlet, and said housing having an outlet;
an intermediate cone-like wall in said housing, said intermediate cone wall disposed between said inlet and said outlet, a first side of said intermediate wall forming a wall support surface, said intermediate cone wall's first side having a contact support surface;
said intermediate wall having a thickness, and said intermediate wall having a second side disposed opposite to said first side of said intermediate wall and situated at across said thickness of said intermediate wall;
at least one through-hole in said intermediate cone wall, said at least one through-hole passing through said thickness of said intermediate wall from said first side to said second side of said intermediate wall;
said intermediate cone-like wall having a base, said thickness of said intermediate wall being connected to said housing at said base so that said intermediate cone-like wall spans a flow passage in said housing;
a rotary slide valve disposed in said housing;
said rotary slide valve including a cylindrical, axially-extending shaft, said cylindrical, axially-extending shaft having a first end surface inside said housing and proximate to said intermediate cone wall;
a flow-sealing hopper, said hopper having a hopper sealing surface configured to cooperate with said intermediate cone wall's support surface to control fluid flow through said at least one through-hole, said sealing hopper connected to said shaft;
a ball, said ball seated in a recess configured to support it between said first end surface and said contact support surface to produce a point-like locus of bearing contact between said shaft and said contact support surface of said intermediate cone wall.

2. A flow control valve as claimed in claim 1, further comprising:
a torsion spring configured to bias said rotary slide valve towards a defined starting position.

3. The flow control valve as claimed in claim 2, wherein:
said torsion spring is disposed around said cylindrical, axially-extending shaft.

4. The flow control valve as claimed in claim 1, wherein:
said torsion spring exerts bias pressing said sealing hopper against said intermediate cone wall.

5. A flow control valve as claimed in claim 1, further comprising:
an actuating motor configured to controllably rotate said rotary slide valve, said actuating motor being operatively connected to said cylindrical, axially-extending shaft.

6. A flow control valve as claimed in claim 5, further comprising:
an elastic coupling arranged between said rotary slide valve and said actuating motor.

7. The flow control valve as claimed in claim 1, wherein:
said intermediate wall sealing surface tapers at an angle between 60° and 120°.

8. The flow control valve as claimed in claim 1, wherein:
said at least one through-hole has a flow-through cross section that progressively diminishes when said rotary slide valve rotates in a radial direction effecting closure by said hopper sealing surface.

9. A flow control valve as claimed in claim 1, further comprising:
a bead at the periphery of said at least one through-hole, said bead having an edge height that increases in the radial direction towards a closure position of said rotary valve.

10. A flow control valve as claimed in claim 1, further comprising:
a plurality of through-holes in said intermediate cone wall, said plurality of through-holes being mutually situated to effect progressive decrease in total flow-through cross section when said rotary slide valve rotates in a radial direction effecting closure by said hopper sealing surface.

11. The flow control valve as claimed in claim 1, wherein:
said at least one through-hole tapers in a cone shape in the radial direction of closure of said rotary slide valve.

12. The flow control valve as claimed in claim 1, wherein:
a cone radius (r/R) of said wall support surface continuously increases in the direction opposite to the direction of closing of said rotary slide valve.

13. The flow control valve as claimed in claim 1, wherein:
a cone radius (r/R) of said hopper sealing surface continuously increases in the direction opposite to the direction of closing of said rotary slide valve.

14. A ventilator comprising:
an air source;
an air inlet connected to said air source;
a sensor for measuring flow in said air inlet;
a sensor for measuring pressure in said air inlet;

a flow control valve housing in said air inlet, said housing having a valve inlet, and said housing having a valve outlet;

an intermediate cone-like wall in said housing, said intermediate cone wall disposed between said valve inlet and said valve outlet, a first side of said intermediate wall forming a wall support surface, said intermediate cone wall's first side having a contact support surface;

said intermediate wall having a thickness, and said intermediate wall having a second side disposed opposite to said first side of said intermediate wall and situated at across said thickness of said intermediate wall;

at least one through-hole in said intermediate cone wall, said at least one through-hole passing through said thickness of said intermediate wall from said first side to said second side of said intermediate wall;

said intermediate cone-like wall having a base, said thickness of said intermediate wall being connected to said housing at said base so that said intermediate cone-like wall spans a flow passage in said housing;

a rotary slide valve disposed in said housing;

said rotary slide valve including a cylindrical, axially-extending shaft, said cylindrical, axially-extending shaft having a first end surface inside said housing and proximate to said intermediate cone wall;

a flow-sealing hopper, said hopper having a hopper sealing surface configured to cooperate with said intermediate cone wall's support surface to control fluid flow through said at least one through-hole, said sealing hopper connected to said shaft;

a ball, said ball seated in a recess configured to support it between said first end surface and said contact support surface to produce a point-like locus of bearing contact between said shaft and said contact support surface of said intermediate cone wall.

15. A ventilator as claimed in claim 14, further comprising:
said air source including a rotating bellows configured to be driven at constant speed throughout a breathing cycle.

16. A ventilator as claimed in claim 14, further comprising:
a torsion spring configured to bias said rotary slide valve towards a defined starting position, said torsion spring being disposed around said cylindrical, axially-extending shaft.

17. A ventilator as claimed in claim 14, further comprising:
said at least one through-hole has a flow-through cross section that progressively diminishes when said rotary slide valve rotates in a radial direction effecting closure by said hopper sealing surface.

18. A ventilator as claimed in claim 14, further comprising:
a bead at the periphery of said at least one through-hole, said bead having an edge height that increases in the radial direction towards a closure position of said rotary valve.

19. A ventilator as claimed in claim 14, further comprising:
a cone radius (r/R) of said wall support surface continuously increases in the direction opposite to the direction of closing of said rotary slide valve.

* * * * *